US006461841B2

(12) United States Patent
Geueke et al.

(10) Patent No.: US 6,461,841 B2
(45) Date of Patent: Oct. 8, 2002

(54) **L-AMINO ACID OXIDASE FROM *RHODOCOCCUS* SPECIES**

(75) Inventors: Birgit Geueke, Reutershagweg (DE); Werner Hummel, Claudiusstrasse (DE); Andreas Bommarius, Atlanta, GA (US)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/986,536

(22) Filed: Nov. 9, 2001

(65) Prior Publication Data

US 2002/0106753 A1 Aug. 8, 2002

(30) Foreign Application Priority Data

Nov. 9, 2000 (DE) .......................................... 100 55 512

(51) Int. Cl.[7] .......................... C12N 9/06; C12N 11/00; C12P 7/40; A61K 38/44
(52) U.S. Cl. ...................... 435/136; 435/174; 435/280; 435/191; 424/94.4
(58) Field of Search ................................ 435/191, 143, 435/280, 136, 174; 536/23.2; 564/303; 424/94.4

(56) References Cited

U.S. PATENT DOCUMENTS 5,416,019 A 5/1995 Leuchtenberger et al.

OTHER PUBLICATIONS

Juliane Beliczey, et al., Novel ligands derived from S–tyrosine for the enantioselective addition of diethylzinc to aldehydes, Tetrahedron Asymmetry, vol. 8, No. 10, pp. 1529–1530, 1997.

Carsten Bolm, et al., Asymmetrische Dihydroxylierung mit Polyethylenglycolmonomethylether–gebundenen Liganden, Angew. Chem. vol. 109, pp. 773–775, 1997.

Filippo Minutolo, et al., Polymer–Bound Chiral (Salen) Mn(III) complex as Heterogeneous Catalyst in Rapid and Clean Enantioselective Epoxidation of Unfunctionalised Olefins, Tetrahedron Letters, vol. 37, No. 19, pp. 3375–3378, 1996.

Iwao Ojima, Catalytic Asymmetric Synthesis, Wiley–VCH Inc., cover, preface, and 3 pages, 1993.

Dieter Seebach, et al., 146. Polymer–and Dendrimer–Bound Ti–TADDOLates in Catalytic (and Stoichiometric) Enantioselective Reactions: Are Pentacoordinate Cationic Ti Complexes the Catalyticaly Active Species?, Helvetica Chimica Act, vol. 79, pp. 1710–1740, 1996.

O. White, et al., Database EMBL 'Online !, Database accession No. AE001863, XP–002189107, pp. 1–90, "Genome Sequence of the Radioresistant Bacterium Deinococcus Radiodurans R1", Nov. 23, 1999.

O. White, et al., Database EMBL 'Online !, Database accession No. Q9RYN6, XP–002189108, 1 page "Genome Sequence of the Radioresistant Bacterium Deinococcus Radiodurans R1", May 1, 2000.

M. Coudert, et al., Arch. Microbiol., vol. 102, No. 2, XP–001055659, pp. 151–153, "Characterization and Physiological Function of a Soluble L–Amino Acid Oxidase in Corynebacterium", 1975.

N. M. W. Brunhuber, et al., The Journal of Biological Chemistry, vol. 269, No. 23, XP–000942066, pp. 16023–16211, "Cloning, Sequencing, and Expression of Rhodococcus L–Phenylalanine Dehydrogenase Sequence Comparisons to Amino–Acid Dehydrogenases", 1994.

G. Massad, et al., Journal of Bacteriology, vol. 177, No. 20, XP–001055638, pp. 5878–5883, "Proteus Mirabilis Amino Acid Deaminase: Cloning, Nucleotide Sequence and Characterization of AAD", Oct., 1995.

*Primary Examiner*—Rebecca E. Prouty
*Assistant Examiner*—Malgorzata A Walicka
(74) *Attorney, Agent, or Firm*—Oblon, Spivak, McClelland, Maier & Neustadt, P.C.

(57) ABSTRACT

L-amino acid oxidases (L-AAO) from Rhodococcus species and nucleic acids, vectors and microorganisms expressing such L-AAOs. L-AAOs may be used to selectively transform the L-portion of a racemic mixture of an amino acid into keto acid, and thus purify the corresponding D-amino acid.

9 Claims, 2 Drawing Sheets

L-AMINO ACID OXIDASE FROM *RHODOCOCCUS* SPECIES

BACKGROUND OF THE INVENTION

1. Field of the Invention

The present invention relates to an enzyme that occurs in Rhodococcus species. In particular, the invention relates to an L-amino acid oxidase (L-AAO) from Rhodococcus, and particularly to that of *Rhodococcus opacus* DSM 42350 as well as to nucleic acids, vectors and microorganisms encoding or expressing L-AAOs. The L-AAOs of the present invention may be used commercially and industrially, for instance, for the production of keto acids or for the purification of D-amino acids from racemic mixtures of amino acids.

2. Description of Related Art

L-amino acid oxidases isolated from snake venom have been intensively studied. These include, for instance, L-amino acid oxidases from *Crotalus atrox*, see Torii, S., M. Naito, and T. Tsuruo, Apoxin I, a novel apoptosis-inducing factor with L-amino acid oxidase activity purified from Western diamondback rattlesnake venom. J. Biol. Chem. 272 (14):9539–42 (1997); *Crotalus adamanteus* , see Raibekas, A. A. and V. Massey, Primary structure of the snake venom L-amino acid oxidase shows high homology with the mouse B cell interleukin 4-induced FIG. 1 protein. Biochem. Biophys. Res. Commun. 248(3):476–8 (1998); *Calloselasma rhodostoma*, see Ponnundurai, G., M. C. Chung, and N. H. Tan, Purification and properties of the L-amino acid oxidase from Malayan pit viper (*Calloselasma rhodostoma*) venom. Arch. Biochem. Biophys. 313(2):373–8 (1994); *Agkistrodon contortrix laticinctus*, see Souza, D. H., et al., Isolation and structural characterization of a cytotoxic L-amino acid oxidase from *Agkistrodon contortrix laticinctus* snake venom: preliminary crystallographic data. Arch. Biochem. Biophys. 368(2):285–90 (1999); *Bothrops cotiara*, see Pessatti, M., et al., Screening of Bothrops snake venoms for L-amino acid oxidase activity, published erratum appears in Appl. Biochem. Biotechnol. 55(3):276 (December 1995); Appl. Biochem. Biotechnol. 51–52:197–210 (1995); *Lachesis muta muta*, see Sanchez, E. O. and A. Magalhaes, Purification and partial characterization of an L-amino acid oxidase from bushmaster snake (Surucucu Pico de Jaca) *Lachesis muta muta* venom. Braz. J. Med. Biol. Res., 24(3):249–60 (1991); *Pseudechis australis*, see Stiles, B. G., F. W. Sexton, and S. A. Weinstein, Antibacterial effects of different snake venoms: purification and characterization of antibacterial proteins from *Pseudechis australis* (Australian king brown or mulga snake) venom. Toxicon. 29(9):1129–41 (1991).; *Ophiophagus hannah*, see Ahn, M. Y., B. M. Lee, and Y. S. Kim, Characterization and cytotoxicity of L-amino acid oxidase from the venom of king cobra (*Ophiophagus hannah*). Int. J. Biochem. Cell. Biol. 29 (6):911–9 (1997); *Naja naja kaouthia*, see Tan, N. H. and S. Swaminathan, Purification and properties of the L-amino acid oxidase from monocellate cobra (*Naja naja kaouthia*) venom. Int. J. Biochem. 24(6):976–73 (1992).

L-amino acid oxidases are also found in algae, see Ito, K., K. Hori, and K. Miyazawa, Purification and some properties of L-amino acid oxidase from *Amphiroa crassissima Yendo*. Hydrobiologica, 151/152:563–569 (1987); Piedras, P., et al., Purification and characterization of an L-amino-acid oxidase from *Chlamydomonas reinhardtii*. Planta 188:13–18 (1992), the cyanobacteria Synechococcus, see Pistorius, E. K. and H. Voss, Some properties of a basic L-amino-acid oxidase from *Anacystis nidulans*. Biochim. Biophys. Acta. 611(2):227–40 (1980); fungi, see Kusakabe, H., et al., A new antitumor enzyme, L-lysine alpha-oxidase from *Trichoderma viride*. Purification and enzymological properties. J. Biol. Chem. 255(3):976–81 (1980); Le, K. H. and V. R. Villanueva, Purification and characterization of epsilon-N-trimethyllysine L-amino oxidase from *Neurospora crassa*. Biochim. Biophys. Acta. 542(2):288–96 (1978).

They may also be found in certain bacteria, see Cioaca, C. and A. Ivanof, Bacterial amino acid oxidases. I. L-amino acid oxidase and its distribution in bacteria. Arch. Roum. Pathol. Exp. Microbiol. 33(3–4):211–22 (1974); Gamati, S. and J. H. Luong, Production and purification of L-phenylalanine oxidase from *Morganella morganii*. Bioseparation 2(3):147–54 (1991); Li, Q. S., J. J. Xu, and J. J. Zhong, Production of L-glutamate oxidase and in situ monitoring of oxygen uptake in solid state fermentation of Streptomyces sp. N1. Applied Biochemistry and Biotechnology, 62:243–250 (1997); Koyama, H., Purification and characterization of a novel L-phenylalanine oxidase (Deaminating and decarboxylating) from Pseudomonas sp. P-501. J. Biochem. (Tokyo) 92(4):1235–40 (1982); Brearley, G. M., et al., Purification and partial characterization of a broad-range L-amino acid oxidase from *Bacillus corotarum* 2Pfa isolated from soil. Appl. Microbiol. Biotechnol. 41(6):670–676 (1994); Bouvrette, P. and J. H. T. Luong, Isolation, purification, and further characterization of an L-phenylalanine oxidase from *Morganella morganii*. Applied Biochemistry and Biotechnology 48:61–74 (1994). The gene sequences of some L-AAOs are known.

On the other hand, despite the identification of gene sequences for certain types of L-AAOs, it has not been possible to develop an expression system for the quantitative production of L-AAOs. The L-AAO from *Crotalus atrox* is the only enzyme that it was possible to express at all, by means of active heterologous expression, see Torii, S., et al., Molecular cloning and functional analysis of apoxin I, a snake venom-derived apoptosis-inducing factor with L-amino acid oxidase activity, Biochemistry 39 (12):3197–205 (2000). The expression was carried out in human embryonal kidney cell cultures and the active enzyme is present in extracellular form. However, the expression of functional L-AAO from *Crotalus atrox* in *E. coli* was not successful. A reason for this could be the glycosylation processes or other modifications that generally make the expression of functional, eukaryotic proteins in microbial systems difficult or impossible.

The sequence of the prokaryotic L-AAO from Synechococcus was published for the first time in 1995, see Bockholt, R., et al., Partial amino acid sequence of an L-amino acid oxidase from the cyanobacterium Synechococcus PCC6301, cloning and DNA sequence analysis of the aoxA gene. Biochim. Biophys. Acta. 1264(3):289–93 (1995) and was clearly corrected again in 1998 (gi:3341474). Until now, however, there has surprisingly been no information about the actual N-terminus of the active enzyme.

The presumable L-AAO gene from *Bacillus subtilis* is probably not complete in the form in which it can be found in databases, since a large portion of the highly conserved FAD binding site is missing and therefore, the presumed L-AAO gene of *Bacillus subtilis* as shown in databases is probably not complete, see Vallon, O., New sequence motifs in flavoproteins: Evidence for common ancestry and tools to predict structure, Proteins 38(1):95–114 (2000). Similarly, a gene product from *Chromobacterium violaceum* has not yet been proven to be an intact, expressible L-AAO sequence (gi:5802874). In the absence of such information, the search for, and discovery of, a suitable expression system for these prokaryotic L-AAOs has been complicated and unproductive.

Previously known L-AAOs have been used in biosensor technology, see Liu, J. and J. Wang, Remarkable thermostability of bioelectrodes based on enzymes immobilized within hydrophobic semi-solid matrices [In Process Citation]. Biotechnol Appl Biochem. 30(Pt 2):177–83 (1999); Varadi, M., et al., Determination of the ratio of D- and L-amino acids in brewing by an immobilized amino acid oxidase enzyme reactor coupled to amperometric detection. Biosens Bioelectron. 14(3):33540 (1999); Sarkar, P., et al., Screen-printed amperometric biosensors for the rapid measurement of L- and D-amino acids. The Analyst 124:865–870 (1999); Lee, Y. C. and M. H. Huh, Development of a biosensor with immobilized L-amino acid oxidase for determination of L-amino acids. Journal of Food Biochemistry 1999:173–185 (1998).

On a small preparative scale, various L-AAOs have been investigated for the transformation of L-lysine derivatives, see Hanson, R. L., et al., Transformation of N epsilon-CBZL-lysine to CBZ-L-oxylysine using L-amino acid oxidase from *Providencia alcalifaciens* and L-2-hydroxyisocaproate dehydrogenase from *Lactobacillus confusus*. Appl. Microbiol. Biotechnol. 37(5):599–603 (1992), for the transformation of L-methionine, Takahashi, E., et al, D-methionine preparation from racemic methionines by *Proteus vulgaris* IAM 12003 with asymmetric degrading activity. Appl. Microbiol. Biotechnol. 47(2):173–179 (1997), and for the transformation of β-N-methylamino-L-alanine, Hashmi, M. and M. W. Anders, Enzymatic reaction of beta-N-methylaminoalanine with L-amino acid oxidase. Biochim. Biophys. Acta. 1074(1):36–94 (1991).

BRIEF DESCRIPTION OF THE INVENTION

Accordingly, in view of the problems with existing L-AAOs, one object of the present invention is to provide an L-AAO that is easy to produce and that can be produced in a quantity suitable for commercial and industrial uses, such as for the production of keto acids or for the purification of D-amino acids.

The present invention provides an L-AAO from Rhodococcus, preferably from *Rhodococcus opacus*, and most preferably from *Rhodococcus opacus*, strain DSM43250. Rhodococcus species within the scope of the present invention, are bacteria that can be classified in Group 22, Subgroup 1 according to Bergey's Manual of Determinative Bacteriology, 9th Ed., Ed.: Hensyl, W. R., Williams and Williams, Baltimore (1994).

L-amino acid oxidases (L-AAO) from Rhodococcus species are provided. Most advantageously the present invention provides an L-AAO from *Rhodococcus opacus* DSM43250 comprising SEQ ID NO: 2 and biologically active fragments (e.g. fragments with an L-AAO activity) of this sequence.

Yet another object is to provide gene sequences, vectors, microorganisms or host cells that encode or express Rhodococcus L-AAOs or biologically active fragments of such L-AAOs. Moreover, it is also an object of the invention to provide such gene sequences and their complements as probes and primers for the identification or production of other L-AAO sequences.

Other aspects of the invention include methods of using Rhodococcus L-AAOs to produce keto acids or for the isolation or purification of D-amino acids by the removal of L-amino acids. The enzymes according to the invention are particularly well suited for technical use and production of enantiomer-concentrated amino acids.

DETAILED DESCRIPTION OF THE INVENTION

The L-AAOs encompassed by the present invention include isolated and purified L-AAOs from Rhodococcus as well as those that are recombinantly expressed from nucleic acid sequences such as SEQ ID NO: 1, which shows the gene sequence for the L-AAO from *Rhodococcus opacus* DSM 43250. Additionally, the L-AAOs of the present invention include fragments of native or recombinantly-expressed proteins that exhibit a biological activity of an L-AAO. Moreover, functional variants or mutants of L-AAOs are also encompassed. Such variants or mutants may be obtained by conventional mutagenesis of microorganisms expressing an L-AAO, for instance, by chemical or UV treatment or by other mutagenesis protocols as described by *Current Protocols in Molecular Biology*, John Wiley & Sons (1987–2000), see especially Chapter 8. Alternatively, they may be produced by recombinant expression of nucleic acid sequences which hybridize to the nucleic acid of SEQ ID NO: 1 and that encode polypeptides having a biological activity of an L-AAO. For example, hybridization conditions of 5×SSC at a temperature of about 50° to 68° C. can be employed for the hybridization reaction. Washing may be performed using 2×SSC and optionally followed by washing using 0.5×SSC. For even higher stringency, the hybridization temperature may be raised to 68° C. or washing may be performed in a salt solution of 0.1×SSC. Other conventional hybridization procedures and conditions may also be used as described by Current Protocols in Molecular Biology. John Wiley and Sons (1987–2000), see e.g. Chapter 2.

The nucleic acid sequences of the present invention as described above, may be placed into plasmids or vectors. Preferred plasmids and/or vectors include vectors of the pET series, also pKK223-3 and various pUC systems (with artificially inserted ribosomal bonding site). Also preferred are plasmids with rhamnose-inducible or arabinose-inducible promotors. In general, all vectors with inducible or constitutive promotors and with natural or artificial ribosomal bonding sites can be used. Other suitable plasmids and vectors are described in Chapter 1 of *Current Protocols in Molecular Biology*. John Wiley and Sons (1987–2000).

The nucleic acid sequences, vectors and plasmids encoding a Rhodococcus L-AAO of the present invention may be placed in a suitable microorganism or host cell. The type of microorganism or host cell is not particularly limited and may be selected by one with skill in the art, for instance, based on its ability to express the L-AAO. Exemplary microorganisms and host cells are described, for instance, by Chapter 1 of *Current Protocols in Molecular Biology*. John Wiley and Sons (1987–2000). Preferably, a prokaryotic organism is used, when the nucleic acid sequences are derived from Rhodococcus, a bacterium. *Escherichia coli* is particularly preferred as an expression system, and more preferably *E. coli* strains XL 01 blue, JM109, NM522, JM105, RR1, DH5α, TOP10, or HB101 or BL21(DE3) may be used. In principle, every plasmid (vector)/host system known to a person skilled in the art can be used for implementing the invention, in which the gene can be cloned via a corresponding cutting site, i.e. the resulting construct can be transformed. A person skilled in the art may select an appropriate plasmid or vector for use in a particular expression system. An overview of the T7 expression system, for example, is given in Studier et al., Methods Enzymol.185, 61–69 (1990). Other suitable expression systems can be found in the relevant known brochures of the companies Novagen, Promega, New England Biolabs, Clontech, as well as Gibco BRL.

The primers of the present invention which correspond to portions of the gene sequences encoding the L-AAOs of the present invention may be designed or selected by those with skill in the art. Such primers may be designed based on comparisons with known sequences in a particular organism, or by using known codon usage for proteins in a particular organism and reverse "translation" of the amino acid sequence of a particular L-AAO into a nucleic acid sequence conforming to the codon use of the target organism. For instance, in the case of *R. opacus*, the use of codons shown in SEQ ID NO: 1 for the primers shown in SEQ ID NOS:. 3 and 4 have proven to be advantageous. Reference is made to the worldwide website:

kazusa.or.jp/codon/cgi-bin/showcodon.cgi?species= Rhodococcus+opacus+[gbbct]. Identical amino acid sequences of proteins from so-called superfamilies are also helpful for probe design, see Firestine et al., Chemistry & Biology 3: 779–783 (1996). Additionally, a PCR primer may be designed and used to identify and obtain L-AAO-related nucleic acid sequences as described by Chapter 15 of *Current Protocols in Molecular Biology*. John Wiley and Sons (1987–2000).

The starting and end sequences of the gene according to the invention that carry the cutting sites should be viewed as preferred primers. Suitable cutting sites can be found in the brochures mentioned above. Cutting sites of the restriction enzymes, which are not present in the gene sequence, for example, cutting sites resulting from NdeI, HindIII or EcoRI, are especially preferred for the construction of primer sequences.

The probes for L-AAO gene sequences according to the invention may be obtained by conventional methods known to those with skill in the molecular biological arts, for instance, from a gene fragment as described, for instance, Sambrook et al., A Laboratory Manual, Cold Spring Harbor Laboratory Press, New York (1989). In principle, therefore any probes that appear advantageous for this purpose to a person skilled in the art can be used to implement the invention. In the case of L-AAO from *Rhodococcus opacus*, a fragment of the gene according to the invention, with a size of 1209 bp, was amplified using the PCR technique and the two primers. This technique is explained in detail in Saiki et al., Science 239, 487–491 (1988), and therefore would be familiar to a person skilled in the art. Its sequence is shown in SEQ ID NO: 5. This probe served as a part of a probe for finding the Rhodococcus L-AAO gene. In this special case, the probe gene fragment was used together with the DIG marking of the Roche Diagnostics company. Genes encoding other L-AAOs from Rhodococcus species may be obtained by a similar procedure to that used to obtain the L-AAO gene of *R. opacus*.

Conventional methods useful for obtaining L-AAO genes from other Rhodococcus species using the probes or primers of the present invention are described, for instance, by Chapters 5, 6 and 15 of *Current Protocols in Molecular Biology*. John Wiley and Sons (1987–2000). Preferably, L-AAO genes from other Rhodococcus species hybridize under stringent conditions to the probes, primers or nucleic acids of the present invention, and encode polypeptides having an L-AAO activity.

The L-AAOs according to the invention are used for the production of L-amino acids and keto acids. The enzyme according to the invention can also be used to purify D-amino acids from their optical antipodes. For example, chemically produced D-amino acids with a lower degree of optical purity can be transformed into D-amino acids with an extremely high enantiomer concentration. It is especially preferred if this process takes place in an enzyme membrane reactor (DE 199 10 691.6).

The stated enzymes can be used in free form, as homogeneously purified compounds, or as enzymes resulting from recombinant production. Furthermore, the enzymes can also be used when present as a component of an intact host organism, or in combination with a cell mass of the host organism that has been digested and purified to any desired degree of purity. They may also be used when present in cell extracts, such as cell sonicates. It is also possible to use the enzymes in immobilized form, see Bhavender P. Sharma, Lorraine F. Bailey and Ralph A. Messing, "Immobilisierte Biomaterialien—Techniken und Anwendungen [Immobilized biomaterials—Techniques and uses]", Angew. Chem. 94, 836–852 (1982). It is advantageous if immobilization takes place by means of lyophilization, see Dordick et al., J. Am. Chem. Soc. 116: 5009–5010 (1994); Okahata et al., Tetrahedron Lett. 38, 1971–1974 (1997); Adlercreutz et al., Biocatalysis 6: 291–305 (1992). Especially preferred is lyophilization in the presence of surfactant substances, such as Aerosol OT or polyvinyl pyrrolidone or polyethylene glycol (PEG) or Brij 52 (diethylene glycol monocetyl ether) (Goto et al., Biotechnol. Techniques 11: 375–378 (1997). Their use as CLECs is also possible, see St. Clair et al., Angew Chem. Int. Ed. Engl. 39(2): 380–383 (Jan. 2000).

The term enantiomer-concentrated as used in the present invention refers to the presence of one optical antipode in the mixture with the other at >50%.

Within the framework of the invention, amino acid is understood to mean a natural or non-natural α or β amino acid, i.e. that the radical located at the α or β C atom of the α or β amino acid is derived from a natural amino acid, such as those presented in Beyer-Walter, Lehrbuch der organischen Chemie [Textbook of organic chemistry], S. Hirzel Verlag Stuttgart, 22nd edition, p. 822 f. (1991), or furthermore also from corresponding non-natural amino acids, such as those listed in DE1 9903268.8.

As illustrated below, the L-AAOs of the present invention transform racemic mixtures of amino acids in such a way that the L-portion of the mixture is transformed into a keto acid:

The D-portion of the particular amino acid with a high degree of enantiomer purity remains after removal of the corresponding L-form. The separation of the keto acid and D-amino acid can take place according to processes known to a person skilled in the art, for example, by means of selective precipitation in an acidic aqueous solution or by means of ion exchange chromatography.

It is advantageous that the enzyme according to the invention possesses a broad substrate spectrum, so that many natural and non-natural amino acids can be transformed. The equilibrium of the reaction lies far to the right side of the reaction equation, so that the transformation takes place quantitatively. The enzyme contains FAD as a cofactor. However, external cofactor generation is not necessary, since the available oxygen spontaneously oxidizes the FAD and therefore regenerates it.

The $H_2O_2$ that is formed during the reaction described above can be destroyed in a manner known to a person skilled in the art, for example with catalase.

Another important advantage of the L-AAOs of the present invention is that they are simply produced and purified from easily cultivated Rhodococcus species. For example, the L-AAO can be obtained from *Rhodococcus opacus* in only three chromatography steps, without any great activity loss, and with a 67% yield of homogeneous protein. Moreover L-AAOs from Rhodococcus species are stable and can be stored at 4° C. for several months, without any activity loss.

An additional positive effect is founded in the fact that along with the D-amino acid, which has been highly concentrated for the enantiomer, a keto acid is also formed. As an option, this process can therefore also be used for the production of very pure keto acids. These are needed, among other things, in low-nitrogen parenteral feeding. For this purpose, extremely high purity requirements are set for the keto acids, and these are difficult to achieve with chemical processes.

The L-AAOs of the present invention may also be used in products and methods for which L-AAOs are conventionally used, such as in biosensors.

The following examples illustrate particular aspects of the present invention.

EXAMPLES

1) Screening for Bacterial L-amino Acid Oxidase Formation Agents

A large number of bacteria species were investigated with regard to their ability to form L-amino acid oxidases (L-AAO). The bacteria were cultured in a medium suitable for their growth, and the medium top fraction was separated from the bacteria mass by means of centrifugation. A search was made for extracellular and intracellular L-amino acid oxidase activity. To digest the cells, a 40% suspension (1.5 mL buffer per 1 g cells) was produced with the digestion buffer (50 mM triethanolamine (TEA), pH 7.0; 1 mM DTT, 1 ml anti-foaming agent/1 L). 1.2 g glass beads (diameter 0.3 mm) and 700/ $\mu$L of the cell suspension were filled into 1.5 mL Eppendorf reaction flasks, and these were placed in cooled holders of a vibration ball mill (MM2: Retsch Company, Germany). Digestion took place by means of shaking for 10 minutes at an amplitude of 100%, and separation of the cell fragments and the glass beads took place by means of centrifugation. The top fractions (crude extracts) were pipetted off and used for detection of enzyme activity according to the following regulations:

0.2 M TEA-HCl buffer, pH 7.6
0.2 mg/mL o-dianisidine
25 U/mL peroxidase from horseradish (POX)
10 mM L-amino acid (L-alanine, L-phenylalanine, L-glutaminic acid, L-proline, L-valine, and L-lysine)

The measurements were carried out in microtiter plates at 30° C. and 450 nm. The total volume per batch was 200 $\mu$L. Each of the L-amino acids indicated was measured individually. In each instance, 80 $\mu$L of the media top fractions and 10–20, $\mu$L of the crude extracts were used per enzyme reaction (200, $\mu$L total).

To assess the individual bacterial species (Table 1), either the activity was indicated in units (U) (1 U corresponds to the formation of 1 $\mu$Mol $H_2O_2$ or pigment per min), or, if the activity was weak, only the presence of oxidase activity was registered.

TABLE 1

Organisms with L-amino acid activity

| Species | DSM No. | Activity for L-leucine +/− | Activity for L-leucine mU/mL | Protein mg/mL |
|---|---|---|---|---|
| *Rhodococcus opacus*, formerly *Rhodococcus ruber* | 43250 | + | 38 | 20.5 |
| *Rhodococcus erythropolis* | 743 | + |  | 14.5 |
| *Rhodococcus equi*, formerly *Nocardia restricta* | 43199 | + |  | 15.7 |
| *Rhodococcus erythropolis*, formerly *Nocardia calcarea* | 43188 | + |  | 11.7 |
| *Rhodococcus spec.*, formerly *Brevibacterium spec.* | 20165 | + |  | 11.0 |
| *Gordona rubropertinctus* formerly *Rhodococcus corallinus* | 43248 | + |  | 6.9 |

2) Cultivation of *Rhodococcus opacus* DSM 43250

To obtain the enzyme, *Rhodococcus opacus* was cultivated in the following medium: 10 g malt extract; 4 g yeast extract; 4 g glucose; 1 L distilled $H_2O$.

The pH of the solution was adjusted to pH 7.2, then the solution was sterilized for 20 min at 121° C. and 1 bar pressure above atmospheric pressure. The organism was cultivated aerobically. On a 10 L scale, the organism was cultivated at 28° C. in a fermenter (Infors, Bottmingen, Switzerland) at a $pO_2$ above 40%, without pH regulation. After 23 h, 148 g moist cell mass was harvested by centrifugation, at an $OD_{600}$ of 10.7. The cell mass can be stored frozen at −20° C., without any loss of activity being evident after several months.

3) Enzyme Isolation
a) Obtaining Crude Extract

The cells were digested by means of wet grinding with glass beads. For this purpose, the moist bacteria mass (15 g) was suspended in 50 mM TEA-HCl buffer (pH 7.0), so that the concentration of the moist cell mass was 25%. The cell content substances were released from the ice-cooled suspension by means of mechanical digestion using a glass bead mill (SCP disintegrator, Innomed-Konsult AB, Sweden). For this purpose, the grinding container was filled with 100 mL glass beads (diameter 0.3 mm) and the cell suspension. Digestion was carried out at a stirring shaft speed of 3,000 rpm. The cooling mantle was filled with ice water before the start of the run.

15 g moist bacteria mass yielded 45 mL crude extract with a volume activity of 0.035 U/mL and a protein content of 9.4 mg/mL. From this, it can be calculated that approximately 150 units L-amino acid oxidase can be obtained from 10 L fermenter batch.

b) Purification of the Enzyme by Chromatography

The enzyme can be purified by means of ion exchange chromatography, hydrophobic interaction chromatography, and chromatography with hydroxyl apatite as the column material. The crude extract was pumped onto a column (h 5.5×diameter 5 cm) packed with MarcoPrep High Q Support Material (Biorad, Hercules, USA), at a flow velocity of 0.2 mnL/min. The ion exchanger had previously been equilibrated with a buffer, which contained 50 mM TEA-HCl, pH 7.0. The column was subsequently washed out with this buffer, then the enzyme was eluted in starting buffer at a step-by-step gradient of 0 to 0.5 M NaCl. At the beginning of elution, the flow rate was increased to 4 mL/min. The L-amino acid oxidase was eluted with approximately 0.15 M NaCl. The active fractions were combined and mixed with 3.5 M $(NH_4)_2SO_4$ solution, so that the end. concentration of ammonium sulfate was 0.75 M $(NH_4)_2SO_4$. This solution was applied to a column (h 4.2×diameter 2.6 cm) packed with phenyl sepharose 6FF material (Amersham Pharmacia Biotech, Uppsala, Sweden), at a flow velocity of 2 mL/min. The column had first been equilibrated with a 50 mM TEA-HCl buffer, pH 7.0, which contained 0.75 M $(NH_4)_2SO_4$. This column, too, was washed out with buffer after the sample was applied. The enzyme eluted within the step-by-step gradient of 0.75 to 0 M $(NH_4)_2SO_4$ in starting buffer, at 0.5 M $(NH_4)_2SO_4$. The active fractions were combined and a change of buffer was carried out in an ultrafiltration unit that holds 50 mL (Amicon, Boston, USA). For this purpose, an ultrafiltration membrane YM10 with a diameter of 43 mm and an exclusion limit of 10 kDA was used (Amicon, Boston, USA). After the change in buffer, the enzyme was present dissolved in 10 mM potassium phosphate buffer, pH 6.5, with 250 mM NaCl. A column (h 8.3×diameter 1.6 cm) filled with ceramic MacroPrep hydroxyl apatite, Type I (Biorad, Hercules, USA) was equilibrated with the same buffer. After the sample was pumped on at a flow rate of 1.5 mL/min, the column was washed with starting buffer and the enzyme was eluted in a step-by-step gradient of 10 mM to 200 mM potassium phosphate buffer, pH 6.5. The L-amino acid oxidase eluted at a potassium phosphate concentration of 50 mM. The elution buffer also contained 250 mM NaCl and was adjusted to pH 6.5. The active fractions were again re-buffered by means of ultrafiltration in 50 mM glycine NaOH, pH 8.6, and stored at 4° C. The result of the purification steps is summarized in Table 2. The purified enzyme has a specific activity of 4.6 U/mg with L-alanine as the substrate.

TABLE 2

Purification table of the L-amino acid oxidase from *Rhodococcus opacus*. Enzyme test: 0.2 M TEA-HCl, pH 7.6; 10 mM L-ala; 25 U/mL POX; 0.2 mg/mL o-dianisidine; L-AAO: 30° C., 450 nm.

| | Volume (mL) | Total protein | Total activity | Spec. act. (U/mg) | Purification factor | Yield (%) |
|---|---|---|---|---|---|---|
| Crude extract | 25 | 262 | 9.6 | 0.03 | 1 | 100 |
| MacroQ pool | 110 | 17 | 12.6 | 0.74 | 23 | 130 |
| Phenyl sepharose pool | 35 | 2.9 | 8.2 | 2.82 | 88 | 85 |
| Hydroxyl apatite pool | 26 | 1.4 | 6.5 | 4.61 | 144 | 67 |

4) Biological Key Data for the L-amino Acid Oxidase from *Rhodococcus opacus* a) pH dependence of the oxidation process

Figure 1:
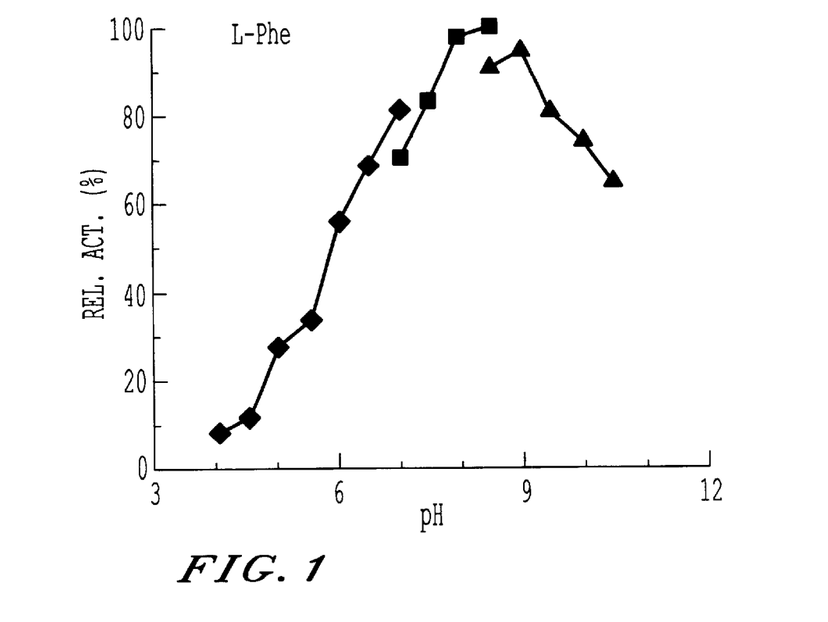
FIG. 1 shows the reaction speed for oxidation of L-phenylalanine (L-Phe) by L-amino acid oxidase (L-AAO) from *Rhodococcus opacus* as a function of pH.
Figure 2:
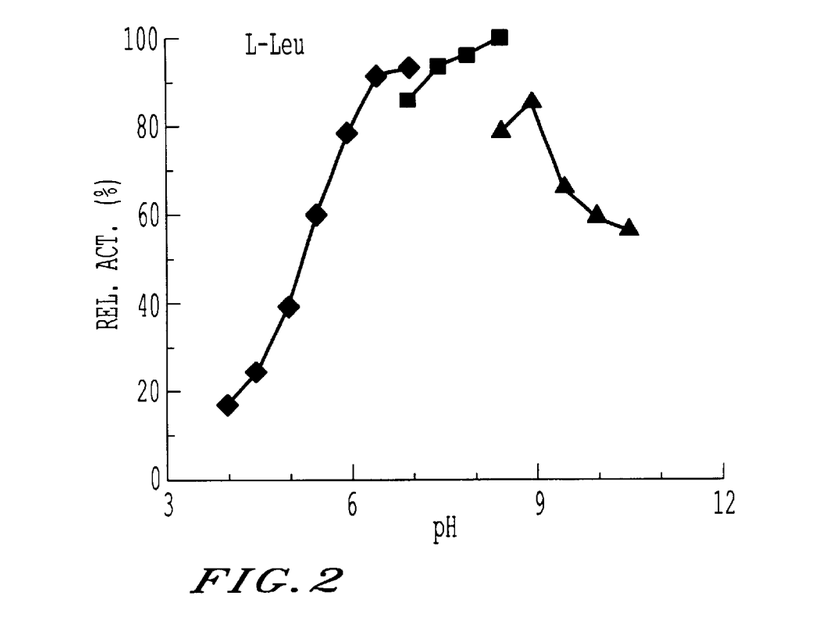
FIG. 2 shows the reaction speed for oxidation of L-leucine (L-Leu) by L-amino acid oxidase (L-AAO) from *Rhodococcus opacus* as a function of pH.
Figure 3:
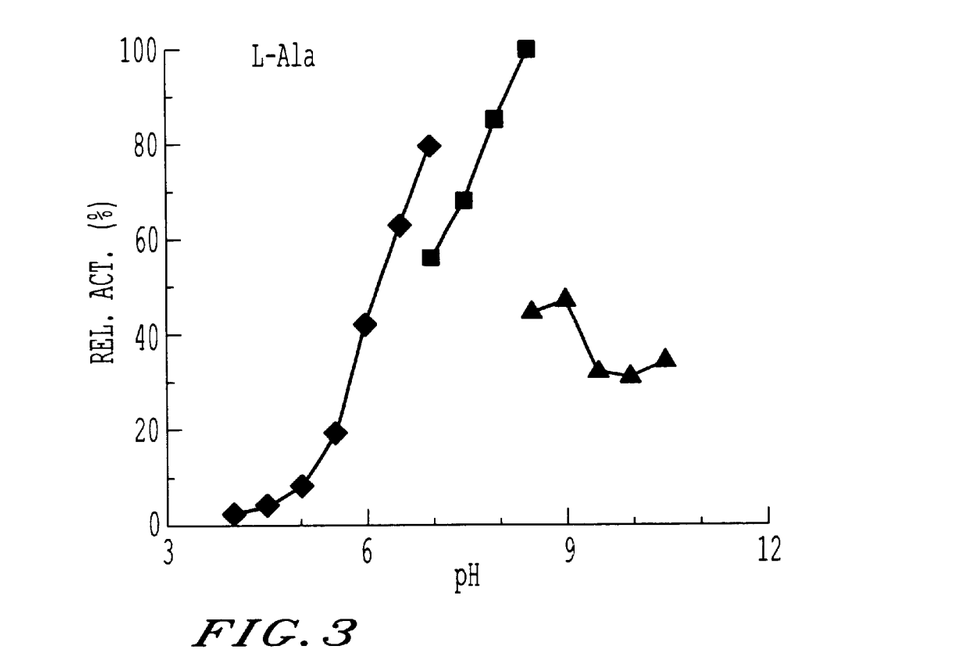
FIG. 3 shows the reaction speed for oxidation of L-alanine (L-Ala) by L-amino acid oxidase (L-AAO) from *Rhodococcus opacus* as a function of pH.

The reaction speed of the oxidation of L-amino acids to keto acids in the presence of the L-amino acid oxidase was studied as a function of the pH in the reaction solution. The test batch (200 μL) had the following composition: 10 mM L-amino acid, 25 U/mL peroxidase from horseradish, 80 mM buffer with different pH values and compositions, 0.2 mg/mL o-dianisidine, enzyme in limiting amount. The enzyme has a pH optimum at pH 8.5 in 80 mM TEA-HCl buffer for L-alanine, L-phenylalanine, and L-leucine (FIG. 1–3: pH optimum of L-amino acid oxidase for the substrates L-phenylalanine (a), L-leucine (b), and L-alanine (c) in different buffers).

b) Storage stability of the L-amino acid oxidase at 4° C.

Under sterile conditions, the purified enzyme can be stored at 4° C. for several months, at a protein concentration of 0.7 mg/mL, in 50 mM glycine NaOH buffer, pH 8.6, without any loss of activity.

c) Storage Stability of the L-amino Acid Oxidase as a Function of the pH L-amino acid oxidase was incubated in 0.2 M buffer of different compositions, at a protein concentration of 24, μg/mL, at room temperature. Afterwards, the residual activity was determined using 0.2 M TEA buffer, pH 7.6, and 10 mM L-ala. This showed a good pH stability in the range of pH 10 to 10.5. After 100 hours in glycine NaOH buffer, it was still possible to detect more than 90% activity at pH 10 and 10.5.

d) Determination of the kinetic constants $K_m$, $K_i$, and $V_{max}$ for various L-amino acids To determine the kinetic constants, the reaction speed of oxidation was studied at different concentrations of amino acid and for different L-amino acids, under the following conditions (tests in microtiter plates):

0.2 M TEA-HCl buffer, pH 7.6; 0.2 mg/mL o-dianisidine; 25 U/mL POX; L-amino acid oxidase in limiting amounts; varying concentrations of the different L-amino acids. Activity measurement was conducted by photometry at 450 nm and 30° C.

The kinetic constants $V_{max}$. $K_m$ and $K_i$ that were found are summarized in Table 3.

TABLE 3

Kinetic data ($K_m$, $K_i$, and $V_{max}$ values) of the enzymatic oxidation of various L-amino acids.

| Substrate | Vmax (U/mg) | Km (mM) | Ki (mM) |
|---|---|---|---|
| L-Ala | 4.27 | 0.274 | — |
| L-Arg | 8.12 | 0.070 | 5.42 |

TABLE 3-continued

Kinetic data ($K_m$, $K_i$, and $V_{max}$ values) of the enzymatic oxidation of various L-amino acids.

| Substrate | Vmax (U/mg) | Km (mM) | Ki (mM) |
|---|---|---|---|
| L-Asn | 5.37 | 0.028 | — |
| L-Cit | 5.47 | 0.026 | 20.6 |
| L-Gln | 5.06 | 0.085 | — |
| L-Glu | 2.32 | 0.411 | — |
| L-Ile | 2.84 | 5.11 | — |
| L-Leu | 6.45 | 0.028 | 5.69 |
| L-Lys | 3.56 | 0.015 | 63.7 |
| L-Met | 6.43 | 0.039 | 6.84 |
| L-Orn | 7.48 | 0.034 | 12.5 |
| L-Phe | 5.64 | 0.019 | 5.29 |
| L-Ser | 4.36 | 1.36 | 192 |
| L-Val | 1.93 | 3.73 | — | e) Substrate spectrum

The transformation of a large number of natural and non-natural amino acids was investigated. The following test batch (1 mL) was used for this purpose: 10 mM enantiomer-pure amino acid (or 20 mM D,L-amino acid); 0.2 M TEA-HCl buffer, pH 7.6; 0.2 mg/mL odianisidine; 10 U/mL POX; L-amino acid oxidase solution in limiting amounts. The activity measurements were carried out by photometry at 436 nm and 30° C.

The stereospecificity of the L-amino acid oxidase was measured for several substrates (e.g. alanine, asparagine, glutamine, phenylalanine, methionine, leucine, ornithine, lysine, histidine), in that both the D-form and the L-form, as well as the racemate were used. In this connection, D-amino acids are not transformed in any case. The activities with the racemates were as high, for all the substrates, as for the pure L-amino acids in each instance. This shows that L-amino acid oxidase is not inhibited by D-amino acids. In the determination of the substrate spectrum, it is therefore also possible to use the D,L-form.

The measured activity values were indicated as relative values with reference to the activity with 10 mM L-alanine (Table 4). Weak activity was indicated with a + in the table.

TABLE 4

Substrate specificity of L-amino acid oxidase
The amino acids marked with * could be used only in low concentrations, because of their poor solubility in water.
Here, 100 µL of the top fraction of a saturated L-amino acid solution were used per test batch.
The amino acids marked with # were used in racemic form.

| | L-amino acid | Rel. activity (%) |
|---|---|---|
| Aliphatic amino acids | Alanine | 100 |
| | Leucine | 68 |
| | Valine | 32 |
| | Isoleucine | 45 |
| | Norleucine# | 73 |
| | Neopentyl glycine | 46 |
| | 2-amino-5,5-dimethyl hexanic acid | 44 |
| Aromatic amino acids | Phenylalanine | 53 |
| | Tyrosine* | 54 |
| | Histidine | 36 |
| | Tryptophan | 12 |
| | Homophenylalanine*# | 50 |
| | Phenyl glycine* | 5 |
| | 2-chlorophenylalanine | 24 |
| | 4-chlorophenylalanine | 9 |
| | 4-fluorophenylalanine# | 25 |
| | 4-nitrophenylalanine* | 30 |
| | 4-aminophenylalanine | 16 |
| | 3-(1-naphthyl)alanine* | 109 |
| | 3-(1-pyridyl)alanine# | 24 |
| Basic amino acids | Arginine | 70 |
| | Lysine | 55 |
| | Glutamine | 52 |
| | Asparagine | 97 |
| | Ornithine | 117 |
| | Citrulline | 74 |
| | Nε-acetyllysine | 46 |
| | 2,3-diaminopropionic acid | 71 |
| | 2,4-diaminobutyric acid | 100 |
| Cyclic amino acids | Homocysteine thiolactone | 23 |
| | 2-amino-4-butyrolactone | 66 |
| containing S/O Amino acids | Serine | 72 |
| | Methionine | 72 |
| | Cystine* | 104 |
| | Cysteinic acid | 34 |
| | O-methyl serine# | 99 |
| | β-Phenyl serine# | 8 |
| Acidic amino acids | Glutaminic acid | 52 |
| | Asparaginic acid | 11 |
| β-amino acids | β-homophenylalanine | + |
| | β-homoalanine | + |

5) Protein Chemistry Key Data of the L-amino Acid Oxidase from *Rhodococcus opacus* a) Determination of the molecular weight of the L-amino acid oxidase and determination of subunits The molecular weight of the native enzyme was determined by means of gel filtration with Superdex 200 PG (Amersham Pharmacia, Uppsala, Sweden). The column (h 61.5×diameter 1.6 cm), coupled to a FPLC system, was operated at a flow rate of 1 mL/min, with 0.95 mL of the highly purified enzyme, with a protein concentration of 0.7 mg/mL, being applied as a sample. Ribonuclease A, chymotrypsinogen, ovalbumin, bovine albumin, aldolase, catalase, ferritin, thyroglobulin were used as calibration proteins. Using these calibration proteins, a molecular weight of 99 kDa was determined for the native oxidase, using this method.

Using gel electrophoresis in a 10% acrylamide gel, in the presence of sodium dodecyl sulfate (SDS), it was possible to determine the size and number of subunits of the enzyme. Accordingly, the molecular weight of the subunit is 57.7 kDa. Phosphorylase B, bovine serum albumin, aldolase, triosephophosphate isomerase, trypsin inhibitor, lysozyme were used for the calibration. Accordingly, the L-amino acid oxidase is made up of two identical subunits. The size, calculated from the sequence (see Example 5c) was 53348 Da.

b) Determination of the isoelectric point

The isoelectric point of the L-amino acid oxidase was determined using isoelectric focusing with carrier ampholytes on agarose, in a pH range of 4–6. The pI is at pH 4.8. Carboanhydrase, β-lactoglobulin, trypsin inhibitor, glucose oxidase were used as marker proteins.

c) Determination of the protein sequence and gene sequence

The highly purified L-amino acid oxidase was transferred from a 10% acrylamide gel containing SDS to a polyvinylidene fluoride membrane, in accordance with the protocol of Kyse and Anderson, then the protein was sequenced to the N-terminal by means of automated Edman decomposition. An Automated Sequences 4774 (Applied Biosystems) with on-line HPLC 120 A was used.

To obtain additional, internal sequences, 200 µg of the homogeneously purified enzyme were split enzymatically, using LysC protease (from Lysobacter enzymogenes). The peptides were separated by way of preparative RP-HPLC (column: Nucleosil 100-5 C8 ET 250/4 (Macherey-Nagel, Duren, Germany), flow agent A: 0.1% trifluoroacetic acid, flow agent B: 0.085% trifluoroacetic acid+84% acetonitrile, detector: 215 nm) and also sequenced for the N-terminal. Proceeding from this sequence information, it was possible to amplify approximately 80% of the L-amino acid oxigenase gene via PCR. This fragment was marked with digoxigen and used as a probe in a hybridization process according to Southern. Genomic DNA from *Rhodococcus opacus*, which had been digested with the restriction enzyme SmaI, resulted in a signal at 3.4 kb in the detection reaction, after separation via an agarose gel and transfer to a nylon membrane. Cloning of SmaI-cut DNA of this size into a pUC18 vector, with subsequent transformation in *E. coli* XL 1 blue, result in a clone that carried the desired fragment. The gene sequence and the protein sequence derived from it can be found in the appendix.

6) Use of the L-amino Acid Oxidase from *Rhodococcus opacus* for the Production of D-amino Acids A 7 mM solution of D,L-phenylalanine was transformed with L-amino acid oxidase (35 µg/mL homogeneous enzyme) in 80 mM TEA buffer, pH 7.6, with 2,600 U/mL catalase being added. The total volume of the batch was 1 mL. Samples (50 µL) were taken at regular intervals, and analyzed for the content of L- and D-phenylalanine, using HPLC. Directly after being taken, the samples were heated to 95° C. for 3 min, and then the precipitated protein was centrifuged off. 20 µL of the diluted top fraction were put into 180 µL 100 mM sodium borate buffer, pH 10.4, and mixed with 20 µL of a derivativization reagent (260 mM isobuturyl-L-cysteine (IBLC) and 170 mM ophthaldialdehyde (OPA) in 100 mM sodium borate buffer, pH 10.4).

Parallel to this, a batch with a 7 mM solution of D,L-leucine was also produced, and the method of procedure as described above was followed.

Separation conditions of HPLC:
Column: RP-18, 250×4 mm, 5 Am, Kromasil (Phenomenex, Aschaffenburg, Germany)
Detection: fluorescence, Ex. 340 nm, Em. 440 nm
Flow agent A: 23 mM sodium acetate buffer; pH 6.5 adjusted with acetic acid
Flow agent B: acetonitrile:water (10:1.5)

Figure 4:
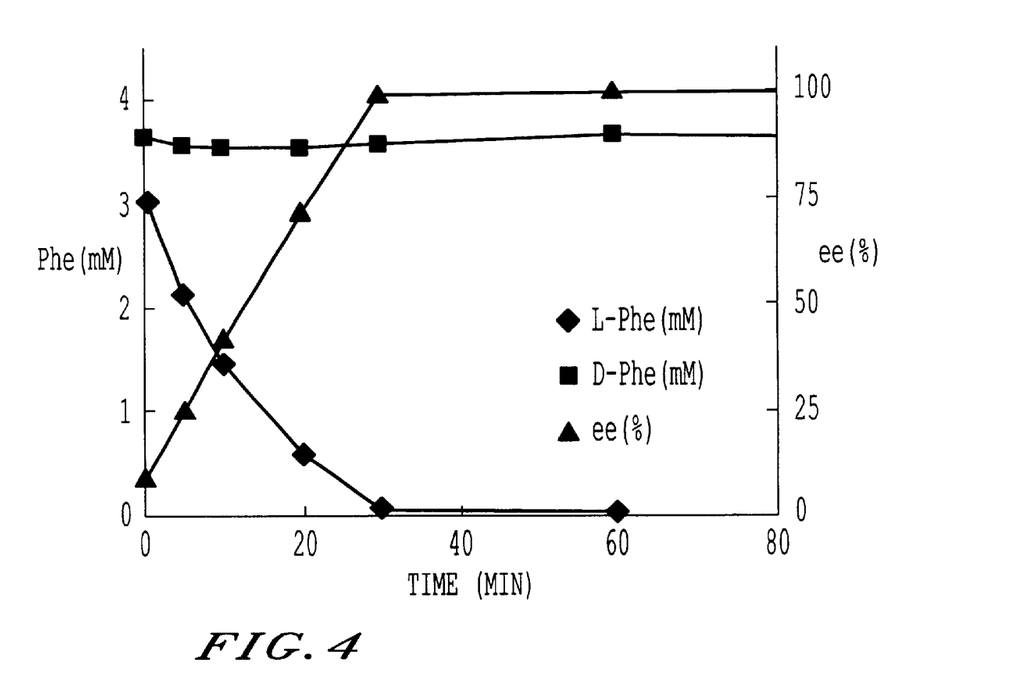
FIG. 4 illustrates the specificity of L-amino acid oxidase (L-AAO) from *Rhodococcus opacus* for L-phenylalanine (L-Phe). L-phenylalanine was essentially removed after about 30 mins, while the concentration of D-phenylalanine was unaffected.

FIG. 4 shows that during the course of the reaction, L-phenylalanine decreases from originally 3.5 mM to <0.01 mM, while the concentration of D-phenylalanine remains constant. The ee value for D-phenylalanine is ≧99.2% after a reaction time of 30 min, and ≧99.5% after a reaction time of 180 min.

L-leucine is almost completely transformed during the first 20 min. At the same time, the concentration of D-leucine remains constant. After a reaction time of 20 min, an ee value of ≧99.2% was measured.

Modifications and Other Embodiments

Various modifications and variations of the described L-amino acid oxidases, and the nucleic acids encoding L-AAOs, as well compositions and methods of their use, and the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the fields of enzymology, biochemistry, microbiology, molecular biology, chemistry, chemical engineering or in related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Priority document German Patent Application 100 55 512.8, filed Nov. 9, 2000 is hereby specifically incorporated by reference.

What is claimed is:

1. An isolated L-amino acid oxidase (L-AAO) from *Rhodococcus* or a fragment or variant thereof that has L-amino acid oxidase activity, wherein said L-AAO is encoded by a DNA molecule hybridizing to SEQ ID NO: 1 at a temperature of about 500° to 680° C. in the presence of 5×SSC followed by washing with 2×SSC to 0.1 SSC.

2. The L-AAO of claim 1, wherein said L-AAO is that of *Rhodococcus opacus* described by amino acid sequence of SEQ ID NO: 2.

3. The L-amino acid oxidase (L-AAO) of claim 1, wherein said L-AAO is that of *Rhodococcus opacus* DSM43250.

4. The L-AAO of claim 1, wherein said L-AAO is in immobilized form or attached to a solid substrate.

5. A composition comprising the L-AAO of claim 1 and a pharmaceutically acceptable carrier or excipient.

6. A method for producing a keto acid comprising:

contacting an L-amino acid with the L-AAO of claim 1 for a time and under conditions suitable for the production of a a keto acid.

7. The method of claim 6 that is carried out in an enzyme-membrane reactor.

8. A method for purifying a D-amino acid from its optical antipode comprising: contacting a mixture of D- and L-amino acids with the L-AAO of claim 1 for a time and under conditions suitable for the production of a keto acid, and separation of the keto acid and D-amino acid.

9. The method of claim 8 that is carried out in an enzyme-membrane reactor.

* * * * *

SEQUENCE LISTING

<160> NUMBER OF SEQ ID NOS: 5

<210> SEQ ID NO 1
<211> LENGTH: 1470
<212> TYPE: DNA
<213> ORGANISM: Rhodococcus opacus
<220> FEATURE:
<221> NAME/KEY: CDS
<222> LOCATION: (1)..(1470)
<223> OTHER INFORMATION:

<400> SEQUENCE: 1

```
gcc ggc gac ctg atc ggc aag gtg aag ggc agc cat tcc gtg gtc gtg       48
Ala Gly Asp Leu Ile Gly Lys Val Lys Gly Ser His Ser Val Val Val
1               5                   10                  15 ctc ggc ggc ggc ccc gcc ggt ctg tgt tcg gca ttc gaa ctg cag aag       96
Leu Gly Gly Gly Pro Ala Gly Leu Cys Ser Ala Phe Glu Leu Gln Lys
            20                  25                  30 gcc ggg tac aag gtg acg gtc ctc gag gcc cgc acc cgg ccc ggt ggc      144
```

```
Ala Gly Tyr Lys Val Thr Val Leu Glu Ala Arg Thr Arg Pro Gly Gly
             35                  40                  45 cgc gtc tgg acc gca cgg ggc agc gag gag acc gac ctg agc ggc         192
Arg Val Trp Thr Ala Arg Gly Gly Ser Glu Glu Thr Asp Leu Ser Gly
 50                  55                  60 gag acg cag aag tgc acg ttc tcg gag ggc cac ttc tac aac gtc ggc     240
Glu Thr Gln Lys Cys Thr Phe Ser Glu Gly His Phe Tyr Asn Val Gly
 65                  70                  75                  80 gcc acc cgc atc ccg cag agc cac atc acg ctc gac tac tgc cgc gaa    288
Ala Thr Arg Ile Pro Gln Ser His Ile Thr Leu Asp Tyr Cys Arg Glu
                     85                  90                  95 ctc ggc gtc gag atc cag gga ttc gga aac cag aac gcc aac acg ttc    336
Leu Gly Val Glu Ile Gln Gly Phe Gly Asn Gln Asn Ala Asn Thr Phe
                100                 105                 110 gtg aac tac cag agc gac acg tcg ctg tct ggc cag tcc gtc acc tac    384
Val Asn Tyr Gln Ser Asp Thr Ser Leu Ser Gly Gln Ser Val Thr Tyr
            115                 120                 125 cgg gcc gcg aag gcc gac acg ttc ggc tac atg tcg gaa ctg ctg aag    432
Arg Ala Ala Lys Ala Asp Thr Phe Gly Tyr Met Ser Glu Leu Leu Lys
    130                 135                 140 aag gcc acc gat cag ggt gcc ctg gat cag gta ctg agc cgg gag gac    480
Lys Ala Thr Asp Gln Gly Ala Leu Asp Gln Val Leu Ser Arg Glu Asp
145                 150                 155                 160 aag gat gcg ctg tcg gag ttc ctc agc gac ttc ggt gac ctg tcc gac    528
Lys Asp Ala Leu Ser Glu Phe Leu Ser Asp Phe Gly Asp Leu Ser Asp
                165                 170                 175 gac ggc cgc tac ctc gga tcc tcg cgt cgc ggt tac gat tcc gag ccc    576
Asp Gly Arg Tyr Leu Gly Ser Ser Arg Arg Gly Tyr Asp Ser Glu Pro
            180                 185                 190 gga gcc ggc ctg aac ttc ggc acc gag aag aag ccg ttc gcg atg cag    624
Gly Ala Gly Leu Asn Phe Gly Thr Glu Lys Lys Pro Phe Ala Met Gln
    195                 200                 205 gaa gtg atc cgc agc ggc atc ggc cgc aac ttc agc ttc gac ttc ggc    672
Glu Val Ile Arg Ser Gly Ile Gly Arg Asn Phe Ser Phe Asp Phe Gly
    210                 215                 220 tac gac cag gcg atg atg atg ttc acc ccg gtc ggc ggc atg gac cgg    720
Tyr Asp Gln Ala Met Met Met Phe Thr Pro Val Gly Gly Met Asp Arg
225                 230                 235                 240 atc tac tac gcg ttc cag gac agg atc ggc acc gac aac atc gtc ttc    768
Ile Tyr Tyr Ala Phe Gln Asp Arg Ile Gly Thr Asp Asn Ile Val Phe
                245                 250                 255 ggc gcc gag gtg acg tcg atg aag aac gtg tcc gag ggc gtc acc gtc    816
Gly Ala Glu Val Thr Ser Met Lys Asn Val Ser Glu Gly Val Thr Val
            260                 265                 270 gaa tac acc gcc ggc ggc tcg aag aag tcg atc acc gcc gac tac gcg    864
Glu Tyr Thr Ala Gly Gly Ser Lys Lys Ser Ile Thr Ala Asp Tyr Ala
    275                 280                 285 atc tgc acg atc ccg ccg cac ctc gtc gga cga ctg cag aac aat ctg    912
Ile Cys Thr Ile Pro Pro His Leu Val Gly Arg Leu Gln Asn Asn Leu
    290                 295                 300 ccc ggc gac gtg ctc acc gcg ctg aag gcg gcc aag ccg tcg tcg tcc    960
Pro Gly Asp Val Leu Thr Ala Leu Lys Ala Ala Lys Pro Ser Ser Ser
305                 310                 315                 320 gga aag ctc ggc atc gag tac tcg cgc cgg tgg tgg gag acg gag gac   1008
Gly Lys Leu Gly Ile Glu Tyr Ser Arg Arg Trp Trp Glu Thr Glu Asp
                325                 330                 335 cgc atc tac ggc ggc gcg tcc aac acc gac aag gac atc tcg cag atc   1056
Arg Ile Tyr Gly Gly Ala Ser Asn Thr Asp Lys Asp Ile Ser Gln Ile
            340                 345                 350
```

```
atg ttc ccg tac gac cac tac aac tcc gat cgc ggt gtg gtc gtc gcc    1104
Met Phe Pro Tyr Asp His Tyr Asn Ser Asp Arg Gly Val Val Val Ala
        355                 360                 365 tac tac agc agc ggc aag cgt cag gag gcg ttc gag tcc ctc acg cac    1152
Tyr Tyr Ser Ser Gly Lys Arg Gln Glu Ala Phe Glu Ser Leu Thr His
370                 375                 380 cgc cag cgg ctc gcc aag gcg atc gcg gag ggc tcg gag atc cac ggc    1200
Arg Gln Arg Leu Ala Lys Ala Ile Ala Glu Gly Ser Glu Ile His Gly
385                 390                 395                 400 gag aag tac acc cgc gac atc tcg tcg tcg ttc tcg ggc agc tgg cgg    1248
Glu Lys Tyr Thr Arg Asp Ile Ser Ser Ser Phe Ser Gly Ser Trp Arg
                405                 410                 415 cgc acc aag tac tcc gag agt gcc tgg gcc aac tgg gcg ggc agt ggc    1296
Arg Thr Lys Tyr Ser Glu Ser Ala Trp Ala Asn Trp Ala Gly Ser Gly
            420                 425                 430 gga tcg cac ggc ggg gcg gcc act ccc gag tac gag aag ctg ctc gaa    1344
Gly Ser His Gly Gly Ala Ala Thr Pro Glu Tyr Glu Lys Leu Leu Glu
        435                 440                 445 ccc gtc gac aag atc tat ttc gcc ggc gac cac ctg tcc aac gcc atc    1392
Pro Val Asp Lys Ile Tyr Phe Ala Gly Asp His Leu Ser Asn Ala Ile
    450                 455                 460 gcc tgg cag cac ggc gcc ctg acg tcc gcc cgc gac gtc gtc acc cac    1440
Ala Trp Gln His Gly Ala Leu Thr Ser Ala Arg Asp Val Val Thr His
465                 470                 475                 480 atc cac gag cgc gtg gcc cag gaa gcc tga                            1470
Ile His Glu Arg Val Ala Gln Glu Ala
                485

<210> SEQ ID NO 2
<211> LENGTH: 489
<212> TYPE: PRT
<213> ORGANISM: Rhodococcus opacus

<400> SEQUENCE: 2

Ala Gly Asp Leu Ile Gly Lys Val Lys Gly Ser His Ser Val Val
1               5                   10                  15

Leu Gly Gly Gly Pro Ala Gly Leu Cys Ser Ala Phe Glu Leu Gln Lys
                20                  25                  30

Ala Gly Tyr Lys Val Thr Val Leu Glu Ala Arg Thr Arg Pro Gly Gly
            35                  40                  45

Arg Val Trp Thr Ala Arg Gly Gly Ser Glu Glu Thr Asp Leu Ser Gly
        50                  55                  60

Glu Thr Gln Lys Cys Thr Phe Ser Glu Gly His Phe Tyr Asn Val Gly
65                  70                  75                  80

Ala Thr Arg Ile Pro Gln Ser His Ile Thr Leu Asp Tyr Cys Arg Glu
                85                  90                  95

Leu Gly Val Glu Ile Gln Gly Phe Gly Asn Gln Asn Ala Asn Thr Phe
            100                 105                 110

Val Asn Tyr Gln Ser Asp Thr Ser Leu Ser Gly Gln Ser Val Thr Tyr
        115                 120                 125

Arg Ala Ala Lys Ala Asp Thr Phe Gly Tyr Met Ser Glu Leu Leu Lys
    130                 135                 140

Lys Ala Thr Asp Gln Gly Ala Leu Asp Gln Val Leu Ser Arg Glu Asp
145                 150                 155                 160

Lys Asp Ala Leu Ser Glu Phe Leu Ser Asp Phe Gly Asp Leu Ser Asp
                165                 170                 175

Asp Gly Arg Tyr Leu Gly Ser Ser Arg Arg Gly Tyr Asp Ser Glu Pro
            180                 185                 190
```

-continued

Gly Ala Gly Leu Asn Phe Gly Thr Glu Lys Lys Pro Phe Ala Met Gln
            195                 200                 205

Glu Val Ile Arg Ser Gly Ile Gly Arg Asn Phe Ser Phe Asp Phe Gly
            210                 215                 220

Tyr Asp Gln Ala Met Met Phe Thr Pro Val Gly Met Asp Arg
225                 230                 235                 240

Ile Tyr Tyr Ala Phe Gln Asp Arg Ile Gly Thr Asp Asn Ile Val Phe
                245                 250                 255

Gly Ala Glu Val Thr Ser Met Lys Asn Val Ser Glu Gly Val Thr Val
            260                 265                 270

Glu Tyr Thr Ala Gly Gly Ser Lys Lys Ser Ile Thr Ala Asp Tyr Ala
            275                 280                 285

Ile Cys Thr Ile Pro Pro His Leu Val Gly Arg Leu Gln Asn Asn Leu
            290                 295                 300

Pro Gly Asp Val Leu Thr Ala Leu Lys Ala Ala Lys Pro Ser Ser Ser
305                 310                 315                 320

Gly Lys Leu Gly Ile Glu Tyr Ser Arg Arg Trp Trp Glu Thr Glu Asp
                325                 330                 335

Arg Ile Tyr Gly Gly Ala Ser Asn Thr Asp Lys Asp Ile Ser Gln Ile
                340                 345                 350

Met Phe Pro Tyr Asp His Tyr Asn Ser Asp Arg Gly Val Val Val Ala
            355                 360                 365

Tyr Tyr Ser Ser Gly Lys Arg Gln Glu Ala Phe Glu Ser Leu Thr His
            370                 375                 380

Arg Gln Arg Leu Ala Lys Ala Ile Ala Glu Gly Ser Glu Ile His Gly
385                 390                 395                 400

Glu Lys Tyr Thr Arg Asp Ile Ser Ser Ser Phe Ser Gly Ser Trp Arg
                405                 410                 415

Arg Thr Lys Tyr Ser Glu Ser Ala Trp Ala Asn Trp Ala Gly Ser Gly
                420                 425                 430

Gly Ser His Gly Gly Ala Ala Thr Pro Glu Tyr Glu Lys Leu Leu Glu
            435                 440                 445

Pro Val Asp Lys Ile Tyr Phe Ala Gly Asp His Leu Ser Asn Ala Ile
450                 455                 460

Ala Trp Gln His Gly Ala Leu Thr Ser Ala Arg Asp Val Val Thr His
465                 470                 475                 480

Ile His Glu Arg Val Ala Gln Glu Ala
                485

<210> SEQ ID NO 3
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
atggccggcg acctcatcgg caaggtcaag ggctcgcac                              39

<210> SEQ ID NO 4
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 4

-continued

```
cttggcgagg cgctggcggt gggtgagcga ctctaaggc                    39
```

<210> SEQ ID NO 5
<211> LENGTH: 1209
<212> TYPE: DNA
<213> ORGANISM: ARTIFICIAL SEQUENCE
<220> FEATURE:
<223> OTHER INFORMATION: SYNTHETIC DNA

<400> SEQUENCE: 5

```
atggccggcg acctcatcgg caaggtcaag ggctcgcacg ccggcgacct gatcggcaag      60
gtgaagggca gccattccgt ggtcgtgctc ggcggcggcc ccgccggtct gtgttcggca     120
ttcgaactgc agaaggccgg gtacaaggtg acggtcctcg aggcccgcac ccggcccggt     180
ggccgcgtct ggaccgcacg gggcggcagc gaggagaccg acctgagcgg cgagacgcag     240
aagtgcacgt tctcggaggg ccacttctac aacgtcggcg ccacccgcat cccgcagagc     300
cacatcacgc tcgactactg ccgcgaactc ggcgtcgaga tccagggatt cggaaaccag     360
aacgccaaca cgttcgtgaa ctaccagagc gacacgtcgc tgtctggcca gtccgtcacc     420
taccgggccg cgaaggccga cacgttcggc tacatgtcgg aactgctgaa gaaggccacc     480
gatcagggtg ccctggatca ggtactgagc cgggaggaca aggatgcgct gtcggagttc     540
ctcagcgact tcggtgacct gtccgacgac ggccgctacc tcggatcctc gcgtcgcggt     600
tacgattccg agcccggagc cggcctgaac ttcggcaccg agaagaagcc gttcgcgatg     660
caggaagtga tccgcagcgg catcggccgc aacttcagct tcgacttcgg ctacgaccag     720
gcgatgatga tgttccaccc ggtcggcggc atggaccgga tctactacgc gttccaggac     780
aggatcggca ccgacaacat cgtcttcggc gccgaggtga cgtcgatgaa gaacgtgtcc     840
gagggcgtca ccgtcgaata caccgccggc ggctcgaaga agtcgatcac cgccgactac     900
gcgatctgca cgatcccgcc gcacctcgtc ggacgactgc agaacaatct gcccggcgac     960
gtgctcaccg cgctgaaggc ggccaagccg tcgtcgtccg gaaagctcgg catcgagtac    1020
tcgcgccggt ggtgggagac ggaggaccgc atctacggcg gcgcgtccaa caccgacaag    1080
gacatctcgc agatcatgtt cccgtacgac cactacaact ccgatcgcgg tgtggtcgtc    1140
gcctactaca gcagcggcaa gcgtcaggag cttggcgagg cgctggcggt gggtgagcga    1200
ctctaaggc                                                            1209
```